United States Patent [19]

Tonrey

[11] Patent Number: 5,259,371
[45] Date of Patent: Nov. 9, 1993

[54] ENDOTRACHEAL TUBE AND METHOD OF INTUBATION

[76] Inventor: Francis G. Tonrey, P.O. Box 2157, Corrales, N. Mex. 87048

[21] Appl. No.: 928,757

[22] Filed: Aug. 13, 1992

[51] Int. Cl.⁵ .............................................. A61M 16/00
[52] U.S. Cl. ........................... 128/200.26; 128/200.24; 128/207.14; 128/207.15; 604/264
[58] Field of Search ....................... 128/207.14, 207.15, 128/200.26; 604/264, 278

[56] References Cited

U.S. PATENT DOCUMENTS

| 3,616,799 | 11/1971 | Sparks | 128/207.15 |
| 3,659,611 | 5/1972 | Miller | 128/207.15 |
| 4,211,234 | 7/1980 | Fisher | 128/200.26 |
| 4,690,138 | 9/1987 | Heyden | 128/207.15 |
| 5,000,175 | 3/1991 | Pue | 604/119 |
| 5,038,766 | 8/1991 | Parker | 128/200.26 |

Primary Examiner—C. Fred Rosenbaum
Assistant Examiner—Noelle Kent Gring
Attorney, Agent, or Firm—Eric A. LaMorte

[57] ABSTRACT

The present invention is an endotracheal tube and the corresponding method of utilizing the endotracheal tube in an intubation procedure. The endotracheal tube is orally advanced past the epiglottis of a patient. The endotracheal tube then rests upon the patient's larynx which serves to create a base reference point for the positioning of the endotracheal tube within the trachea of the patient. By knowing how far the endotracheal tube is advanced beyond the point of contact with the larynx, the person administering the intubation procedure can accurately position the end of the endotracheal tube safely within the patient's trachea.

22 Claims, 6 Drawing Sheets

ENDOTRACHEAL TUBE AND METHOD OF INTUBATION

BACKGROUND OF THE INVENTION

1. Field of the Invention

The present invention relates to endotracheal tubes of the type used in the oral intubation of small children, neonate and premature neonate patients, and more particularly to such endotracheal tubes that include a radially extending flange that rests upon the arytenoid cartilages within the larynx of the intubated patient, thereby limiting the depth for which the endotracheal tube can be advanced into the trachea and providing a base point from which the depth of the endotracheal tube below the vocal cords can be measured.

2. Prior Art Description

Accidental right mainstream endotracheal intubation is a common cause of pulmonary morbidity (i.e. lung collapse, hypoxemia, cardiac arrest, etc.) in all patients undergoing an endotracheal intubation procedure. Accidental right mainstream endotracheal intubation occurs when an endotracheal tube is advanced too far within a patient's trachea. In such a situation, the endotracheal tube enters the right bronchi of the lung causing the left lung to collapse. Such accidental right mainstream endotracheal intubation results in many deaths each year and causes surviving patients to incur extensive pulmonary care. The dangers of accidental right mainstream endotracheal intubation is of particular concern during the intubation of small children, neonate and premature neonate patients. With such patients, the physical length of the patient's trachea is very short. Additionally, the lungs of such patients are often weak, leaving the patient particularly susceptible to the disastrous consequences of accidentally advancing an endotracheal tube beyond the trachea and into the bronchi of a lung.

As will be recognized by a person skilled in the art, the trachea lays between the larynx of a patient and the left and right bronchi of a patient's lungs. To properly perform an endotracheal intubation procedure, the distal end of an endotracheal tube must be positioned within the patient's trachea. If the distal end of an endotracheal tube were to move out of the trachea, above the larynx, the vocal cords may close, preventing the intubation of the lungs and possibly causing such consequences as suffocation or should the vocal cords not close, gastric content aspiration could occur. If the distal end of the endotracheal tube descends below the trachea, the endotracheal tube typically enters the right mainstream bronchus of the lung causing the pulmonary morbidity effects previously described.

In the prior art there exist many features designed into endotracheal tubes to assist in positioning the distal end of the endotracheal tube within a patient. One of the most common features designed into prior art endotracheal tubes is the use of distance indicators printed onto the exterior surface of the endotracheal tube. The distance indicators are indicative of the distance between the distal end of the endotracheal tube and the marking itself. For example, if an orally applied endotracheal tube is advanced down a patient's throat until an indication of fifteen centimeters is seen at the patient's mouth, the person administering the endotracheal tube can see that the endotracheal tube has been advanced fifteen centimeters into the patient's mouth and into the patient's throat. By knowing the size of the patient, the person administering the endotracheal tube can estimate the intubation distance needed to position the distal end of the endotracheal tube properly within the patient's trachea. Such estimated positioning is obviously only as accurate as the skills of the person positioning the endotracheal tube. Additionally, endotracheal tubes that rely solely on distance indicators for placement must be used in conjunction with an external endotracheal tube restraint devices to ensure the distal end of the endotracheal tube does not move after it is placed within a patient's trachea.

In the prior art, the exact placement of the endotracheal tube can only be checked via an X-ray image. Consequently, an X-ray imaging device is often used when intubating a patient with an endotracheal tube. The X-ray imaging device allows the person administering the endotracheal tube to place the distal end of the tube in a patient's trachea with greater accuracy. However, such a procedure exposes both the patient and the attending medical personnel to unnecessary dosages of X-ray radiation. Furthermore, X-ray facilities are seldom available on an emergency basis.

Another prior art device that helps in the placement of the distal end of an endotracheal tube in the trachea of a patient is the use of inflatable bladders positioned near the distal end of the endotracheal tube. With such devices, the endotracheal tube is placed down a patient's throat. When the distal end of the endotracheal tube becomes properly positioned within a patient's trachea, the bladder is inflated. The inflated bladder contacts the interior walls of the trachea, substantially anchoring the endotracheal tube into a set position. In the art of endotracheal intubation, such endotracheal tubes that include such inflatable bladders are said to be "cuffed". Cuffed endotracheal tubes have the disadvantage of being both expensive and difficult to manufacture. Furthermore, the inflatable bladder on cuffed endotracheal tubes increases the overall diameter of the distal end of the endotracheal tube. As a consequence, cuffed endotracheal tubes are not preferred on small children, neonate and premature neonate patients. The extremely narrow larynx and trachea of such patient's makes the use of cuffed endotracheal tubes unpractical. Furthermore, since small children, neonate and premature neonate patients have very sensitive trachea walls, the use of cuffed endotracheal tubes with such patients may inflame the tissue within the trachea as the bladder is inflated, thereby causing the risk of the patient's trachea swelling closed or otherwise severely restricting air flow to the lungs.

Since cuffed endotracheal tubes are not desirable for small children, neonate and premature neonate patients, uncuffed endotracheal tubes are commonly used, leaving the person performing the endotracheal intubation to rely solely upon the radiopaque distance indicator lines to properly position the endotracheal tube. Since the length of the trachea in such patients is extremely short, the proper placement of the endotracheal tubes becomes even more of an exacting procedure. Furthermore, the use of X-ray imaging to help in the placement of uncuffed endotracheal tubes is also undesirable because the X-ray radiation produced by the X-ray imaging is an added danger to small children, neonate and premature neonate patients. As a result, medical personnel who want to limit X-ray radiation exposure to their patients are left with little alternative but to visually rely upon the distance indicators of an endotracheal tube outside the patient's body to estimate proper location of the distal end of the endotracheal tube within the trachea of the patient.

In view of the needs that exist in the prior art, it is a primary objective of the present invention to provide an endotracheal tube that provides medical personnel placing the endotracheal tube within a patient, a positive indication that assures the administering personnel that the distal end of the endotracheal tube is properly positioned within a patient's trachea.

It is a further objective of the present invention to provide such an endotracheal tube that is small in size so as to be readily used on small children, neonate or premature neonate patients.

SUMMARY OF THE INVENTION

The present invention is an endotracheal tube and the corresponding method of using the endotracheal tube in intubating a patient. The present invention endotracheal tube includes a flexible conduit that can be orally advanced down the throat of a patient. The flexible conduit has two open ends that provides the means through which the patient's respiration can occur and gases, such as those used for anesthesia, can be introduced into the patient.

In the present invention endotracheal tube a flange is positioned proximate the end of the tube that is advanced into the throat of the patient. The flange is narrow enough to pass beyond the epiglottis of the patient, yet is too wide to pass between the vocal folds within the larynx. As such, the flange contacts the larynx and the advancement of the flexible conduit is stopped. Extending below the flange of the flexible conduit is a smaller flexible tube. The smaller tube is narrow enough to pass between the vocal folds within the larynx and is therefore capable of traversing the larynx and entering the trachea. The smaller tube extends a predetermined distance below the flange. As such, the person administering the intubation procedure knows exactly where the tip of the smaller tube is relative the larynx of the patient. As such, the person administering the intubation procedure can utilize the patient's larynx as a base reference point, thereby allowing the proper positioning of the smaller tube within the patient's trachea.

In the preferred embodiment, a smaller tube is positioned within a larger tube and is reciprocally movable therein. The flange that contacts the patient's larynx radially extends from the outer tube member. As such, when the flange of the outer tube member contacts the patient's larynx, the inner tube member can be advanced beyond the outer tube member and into the patient's larynx. Gases are then introduced and removed from the patient through the lumen of the inner tube member.

Since the placement of the inner tube member beyond the outer tube member is critical to properly positioning the inner tube member within the patient's trachea, a distance indicating means and locking means may be formed as part of the endotracheal tube. The distance indicating means provides the person administering the endotracheal tube with a visual indication showing of the distance by which the inner tube member is extended beyond the flange of the outer tube member. By reading the visual indication, one can be assured that the inner tube member is not over or under extended relative the patient's larynx. The locking means allows the inner tube member to be retained into a set position relative the outer tube member, thereby preventing an inadvertent change in the position of the endotracheal tube within the patient.

BRIEF DESCRIPTION OF THE DRAWINGS

For a better understanding of the present invention endotracheal tube, reference is made to the following description of exemplary embodiments thereof, considered in conjunction with the accompanying drawings, in which.

DETAILED DESCRIPTION OF THE INVENTION

Although the present invention endotracheal tube can be used on any patient undergoing an endotracheal intubation procedure, the present invention endotracheal tube is especially suitable for use in small children, neonate or premature neonate patients. Accordingly, the present invention will be hereinafter described in connection with the endotracheal intubation of a small child, neonate or premature neonate patient and will address the complications conventionally associated with intubation procedures on such patients.

Figure 1:
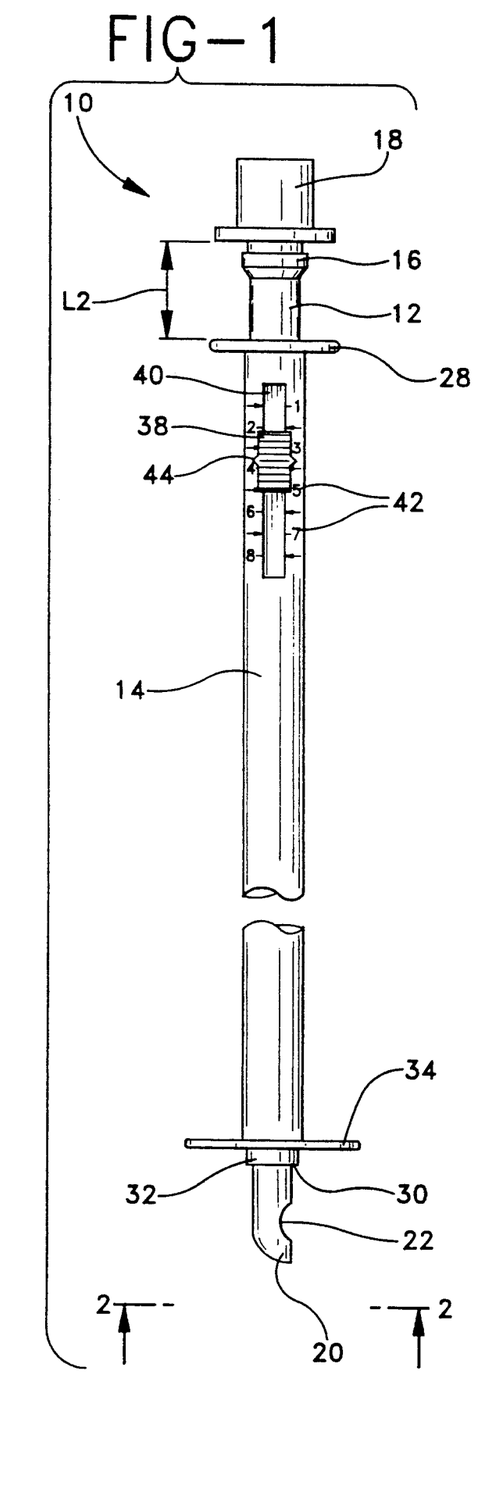
FIG. 1 is a front view of one preferred embodiment of the present invention endotracheal tube.
Figure 2:
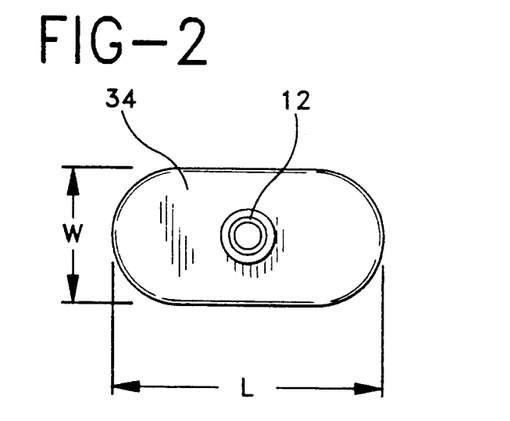
FIG. 2 is a bottom view of the embodiment of the present invention shown in FIG. 1.
Figure 3:
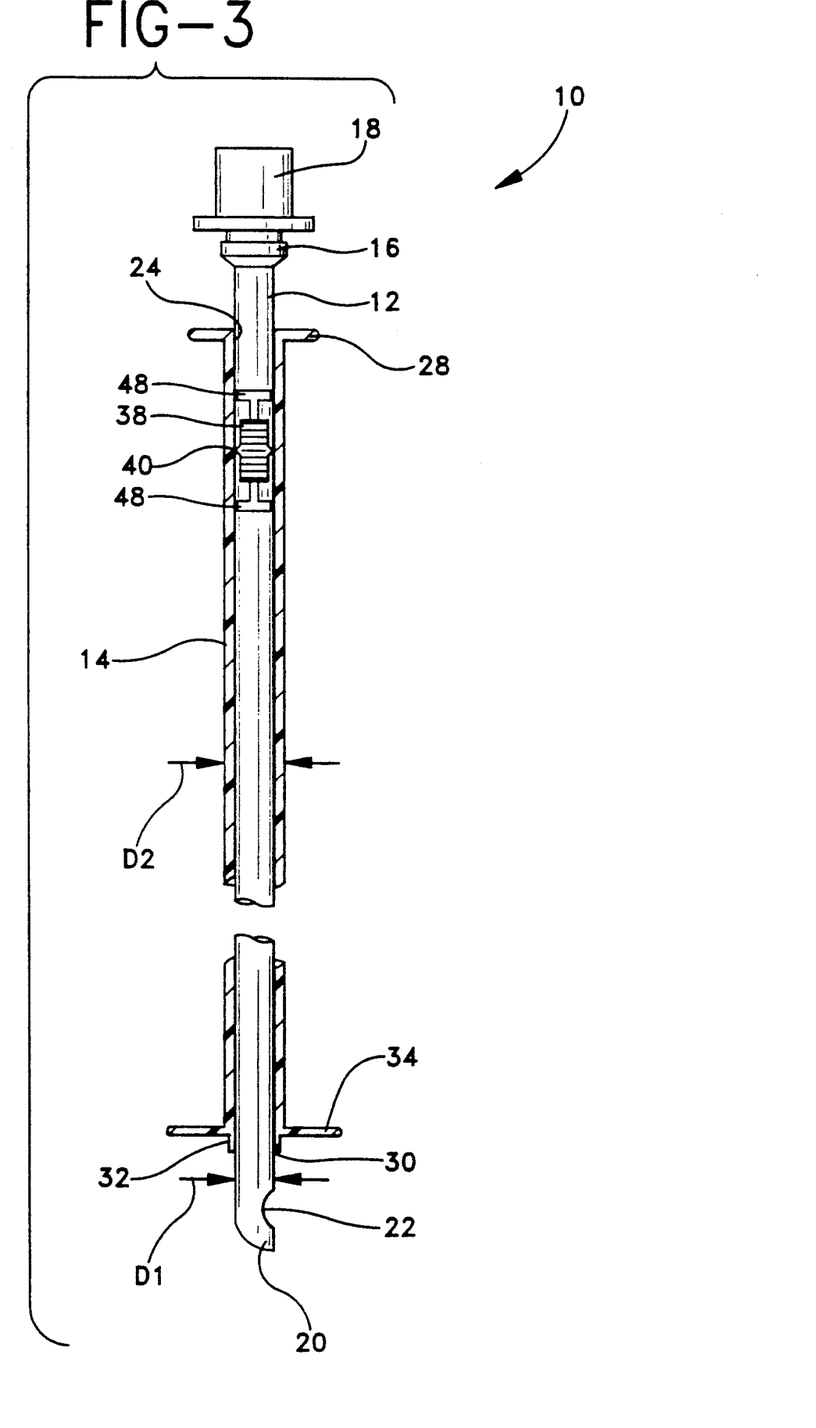
FIG. 3 is a front view of the embodiment of the present shown in FIG. 1 having the top surface removed to show internal elements.

In FIG. 1 there is shown one preferred embodiment of the present invention endotracheal tube 10 comprised essentially of two tubular members wherein an inner tube member 12 is coaxially positioned within a slightly larger outer tube member 14. Both the inner tube member 12 and the outer tube member 14 are formed from a highly flexible material such as a silicon based or a polyvinyl chloride based material, however, any other material known for use in endotracheal tubes may also be employed. The materials selected for the inner and outer tube members 12, 14 may be opaque but are preferably performed from a substantially transparent material which is the standard for endotracheal tubes. Referring to FIGS. 2 and 3 in conjunction with FIG. 1, it can be seen that the inner tube member 12 is continuous, traversing the entire length of the outer tube member 14. The inner tube member 12 has an inner diameter D1 of between 2.0 and 6.0 mm, if formed for a small child or neonate patient. However, it should be understood that the inner tube member 12 may have an inner diameter D1 of up to 10.0 mm if it were fabricated for an adult patient. The inner diameter D2 of the outer tube member 14 is formed to be slightly larger than the diameter of the inner tube member 12. As such, the inner tube member 12 is free to move reciprocally within the confines of the outer tube member 14.

The inner tube member 12 is longer than the outer tube member 14 and has both a supply end 16 for receiving gases and a discharging end 20 for feeding such gases into a patient. The supply end 16 of the inner tube member 12 is coupled to a gas line connector 18 of the type conventionally employed within endotracheal tubes. The gas line connector 18 couples a gas line source (not shown) to the inner tube member 12, thereby allowing gases to flow into, and from, the inner tube member 12. The discharging end 20 of the inner tube member 12 is formed at a tapered angle. Furthermore, an orifice 22 is formed through the wall of the inner tube member 12 at a point proximate the tip of the discharge end 20. As will be recognized by a person skilled in the art, the orifice 22 formed proximate the discharge end 20 creates a structure known in the art as a Murphy eye.

The inner tube member 12 is coaxially positioned within the outer tube member 14, however both the inner tube member 12 and the outer tube member 14 are flexible. Consequently, both the inner tube member 12 and the outer tube member 14 bend together as the present invention endotracheal tube 10 is manipulated. The inner diameter D2 of the outer tube member 14 is only slightly larger than the overall diameter of the inner tube member 12. As such the inner tube member 12 is free to move into, and out of, the outer tube member 14. The outer tube member 14 is substantially tubular having two open ends through which the inner tube member 12 passes. The upper end 24 of the outer tube member 14 faces the gas line connector 18, and may contain a small radial flange 28 to assist a user in gripping the outer tube member 14. The lower end 30 of the outer tube member 14 forms a gas and liquid tight seal around the inner tube member 12, yet allows for the movement of the inner tube member 12 relative the outer tube member 14. The lower end 30 of the outer tube member 14 may include a transition region 32 that diverges toward the inner tube member 12 helping to form the substantially air tight seal between the outer tube member 14 and the inner tube member 12. However, it should be understood that other constructions such as those employing O-rings to create the air tight seal may also be used.

A shaped flange 34 is formed proximate the lower end 30 of the outer tube member 14. The shaped flange 34 extends radially from the longitudinal axis of the outer tube member 14, thereby protruding at a perpendicular to the exterior surface of the outer tube member 14. As can be seen from FIG. 2, the shaped flange 34 is substantially planar and circularly oblong. However, as will later be described, other shapes may be employed. The shaped flange 34 has a width W and a length L that allows the flange 34 to be passed into a patient's throat, past the epiglottis. However, as will later be explained, the length L and width W of the flange 34 are not large enough to pass through the larynx of a patient and enter the trachea.

A finger engagement support 38 is affixed to the exterior of the inner tube member 12 within the confines of the outer tube member 14. The finger engagement support 38 does not confine the flow within the inner tube member 12, yet grips the inner tube member 12 in a manner that prevents the inner tube member 12 from moving independently of the finger engagement support 38. The finger engagement support 38 protrudes out of the confines of the outer tube member 14 through an elongated slot 40 formed in the material of the outer tube member 14. Distance indicators 42, indicative of consecutive measurements in millimeters, are printed on the exterior of the outer tube member 14 on either side of the elongated slot 40. A point indicator 44 may be formed on the finger engagement support 38 to show the position of the finger engagement support 38 relative the printed distance indicators 42. The point indicator 44 may be a pointed protrusions as shown, or may be any other indication such as a line molded into, or printed on, the finger engagement support 38, which may then be aligned with the printed distance indicators 42.

As the finger engagement support 38 is moved back and forth within the elongated slot 40, the inner tube member 12 is forced to move relative the outer tube member 14. The position of the finger engagement support 38 relative the printed distance indicators 42 corresponds to the distance the inner tube member 12 extends below the lower end 30 of the outer tube member 14. For instance, if the point indicator 44 formed on the finger engagement support 38 were aligned with a distance indicator 42 printed on the outer tube member 14 that indicated 5.0 mm, then the discharging end 20 of the inner tube member 12 would extend 5.0 mm below the lower end 30 of the outer tube member 14. As such, it should be understood that the length of the elongated slot 40 formed into the outer tube member 14 controls the length by which the inner tube member 12 can be extended beyond the lower end 30 of the outer tube member 12. The positioning of the elongated slot 40 should always allow for the discharge end 20 of the inner tube member 12 to be fully retracted into the outer tube member 14. That is, the finger engagement support 38 should be positionable within the elongated slot 40 such that the discharge end 20 of the inner tube member 12 can be retracted to a point either flush with, or higher than, the lower end 30 of the outer tube member 14.

The length of the elongated slot 40 is dependent upon the type of patient on which the present invention endotracheal tube 10 is being applied. For instance, with a neonate patient, the inner tube member 12 may only need to be extended 1 mm to 2 mm below the lower end 30 of the outer tube member 14 and into the patient's trachea. As such, only a short slot 40 need be manufactured so as to allow for this range of movement. With adult patients, the inner tube member 12 may have to be extended 5 mm to 8 mm into the trachea, as such a larger slot 40 must be used. Additionally, it should be understood that the distance L2 of the inner tube member 12, above the upper end 24 of the outer tube member 14 and below the gas line connector 18 may also limit the range of movement of the inner tube member 12 relative the outer tube member 14. As such, there should be enough space formed between the upper end 24 of the outer tube member 14 and the gas line connector 18 to allow for the movement of the inner tube member 12 relative the outer tube member 14, throughout the range allotted by elongated slot 40.

Figure 4:
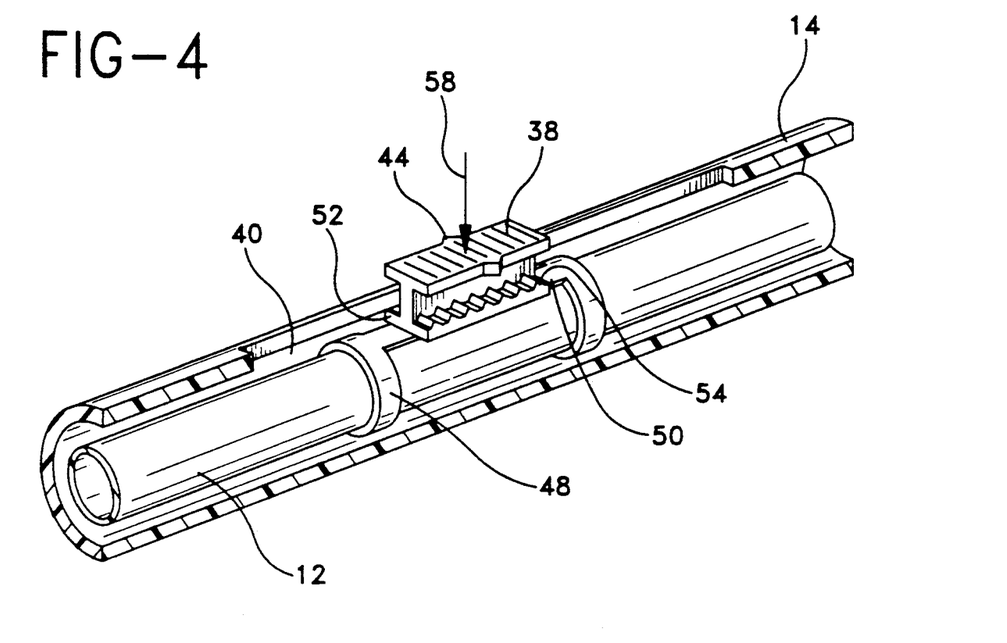
FIG. 4 is a fragmented perspective view of the locking mechanism for the embodiment of the present invention shown in FIG. 1.

In the present invention endotracheal tube 10, it is desirable to have a means whereby the position of the inner tube member 12 can be locked relative the outer member 14, thereby preventing the inadvertent movement of the inner tube member 12 relative the outer tube member 14. Referring to FIG. 4, one preferred embodiment of such a locking means is shown. In FIG. 4, it can be seen that the finger engagement support 38 is formed to have a substantially I-shaped profile, wherein the top section of the finger engagement support 38 projects above the outer tube member 14 and the lower section of the finger engagement support extends into the hollow of the outer tube member 14. Because of the I-shape of the finger engagement support 38, the finger engagement support 38 is trapped within the elongated slot 40, and is unable of being pushed entirely below, or pulled entirely above, the elongated slot 40. Clip prongs 48 encircle and grasp the outside diameter of the inner tube member 12. The clip prongs 48 are formed onto the bottom of a curved spring member 50 which connects the clip prongs 48 to the I-shaped finger engagement support 38. Due to the geometry of the spring member 50, the lower flange 52 of the finger engagement support 38 is biased against the inner surface of the outer tube member 14. Lock projections 54 are formed on the surface of the lower flanges 52 that contacts the outer tube member 14. Consequently, the force of the lock projections 54 against the outer tube member 14 acts to lock the finger engagement 38 into a set position relative the outer tube member 14. Since the finger engagement support 38 is affixed to the inner tube member 12, via the spring member 50 and clip prongs 48, the force of the lock projections 54 against the outer tube member 14 acts to hold the inner tube member 12 into a set position relative the outer tube member 14.

To reciprocally move the inner tube member 12 relative the outer tube member 14, the finger engagement support 38 is depressed in the direction of arrow 58. As such, the mid-region of the I-shaped finger engagement support 38 is forced down into the elongated slot 40 and against the spring bias. The downward force deforms the spring member 50, thereby allowing the lock projections 54 to disengage from the outer tube member 14. With the lock projections 54 disengaged, the inner tube member 12 can be reciprocally moved within the outer tube member 14 by moving the finger engagement support 38 back and forth within the elongated slot 40.

As will be recognized by a person skilled in the art, the described finger engagement support 38 is merely exemplary and there exist many other methods for locking the position of an inner tube relative a surrounding outer tube. For example, an interference fit may be had in between the inner tube member 12 and the outer tube member 14. As such the two tubes would be locked into a set position until a force was applied between the two tubes that overcame the force of friction created by the interference fit. Furthermore, various other known spring bias locking means or adjustable collet devices can be used to hold the inner tube member 12 in a set position relative the outer tube member 14. All such locking means are intended to be covered by the scope of this disclosure.

Figure 5:
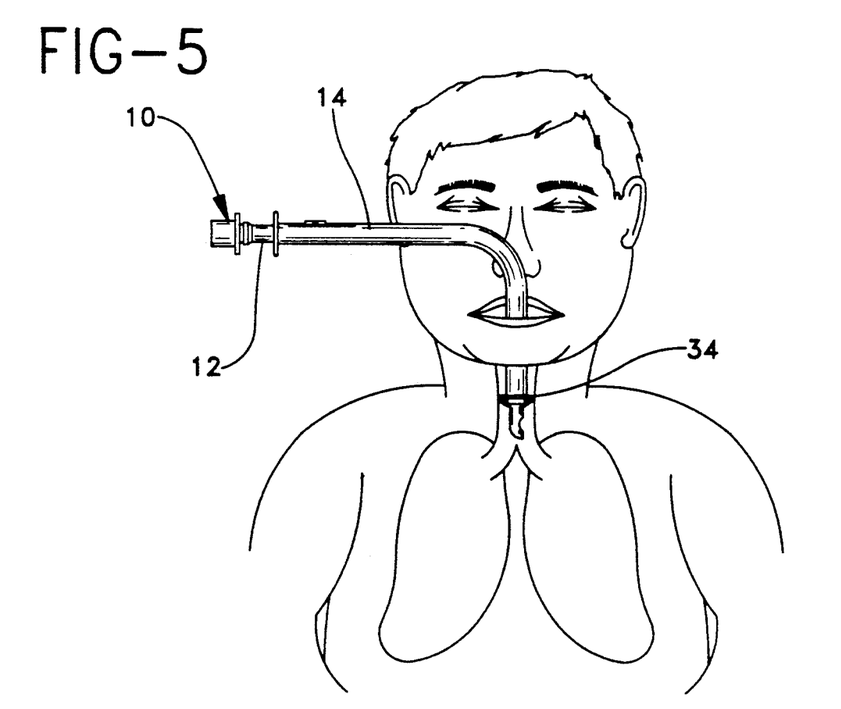
FIG. 5 is a perspective view of the preferred embodiment of the present invention shown in conjunction with a neonate patient to facilitate consideration and discussion.
Figure 6:
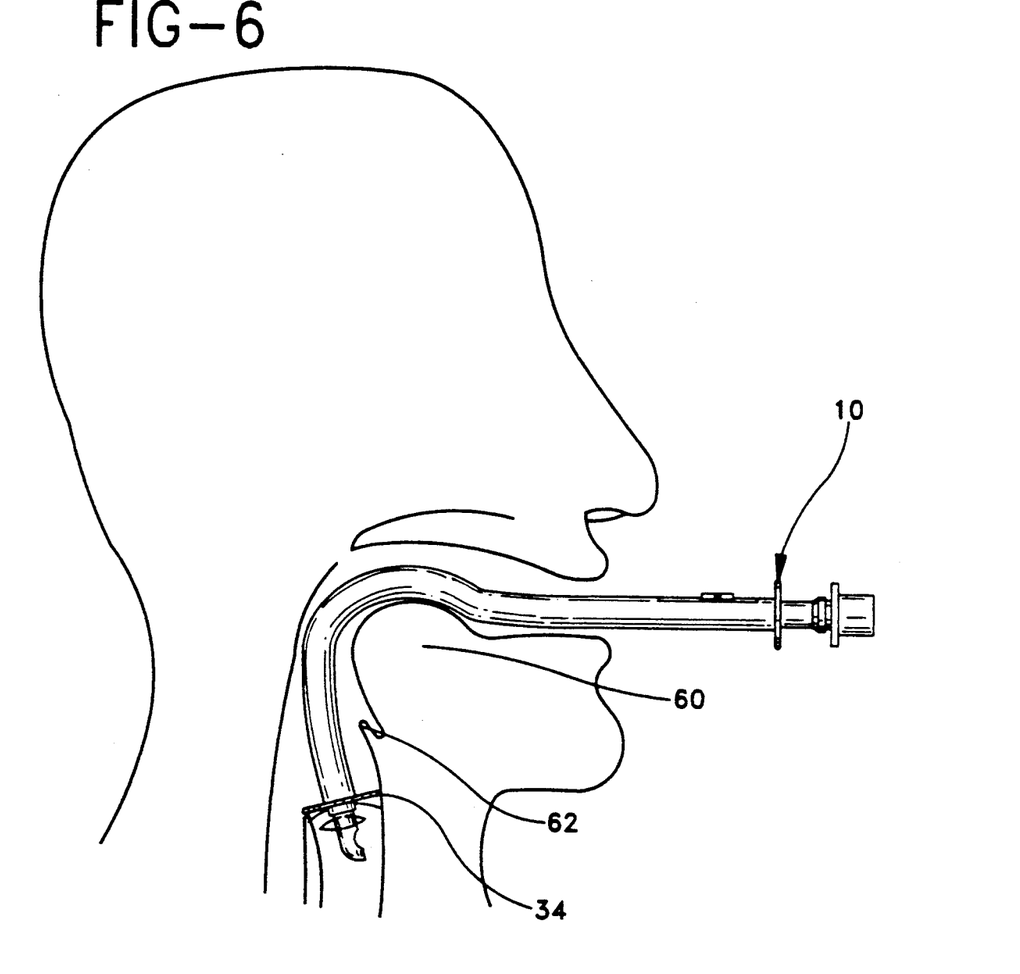
FIG. 6 is a side view of the preferred embodiment of the present invention shown in conjunction with a cross sectioned head and neck of a patient to illustrate the application and function of the present invention.

Referring now to FIGS. 5 and 6, the present invention endotracheal tube 10 is shown in use on a neonate patient. As can be seen, the endotracheal tube 10 is administered orally, passing through the mouth of the patient. When administered, the inner tube member 12 is fully retracted within the outer tube member 14, that is the inner tube member 12 is retracted to a position so that the discharging end 20 of the inner tube member 12 does not extend below the lower end 30 of the surrounding outer tube member 14. At this point, the point indicator 44 on the finger engagement support 38 should align with a distance indicator of zero (0.0) on the outer tube member 14. Additionally, it is at this point that the distance between the gas line connector 18 and the upper end 24 of the outer tube member 14 is also at its maximum. As the endotracheal tube 10 is passed into the patient's mouth, the shaped flange 34 at the lower end 30 of the outer tube member 14 is guided over the tongue 60, past the epiglottis 62 and into the patient's larynx. The positioning of the endotracheal tube 10 into the larynx is done in the conventional manner and may include use of a malleable wire stylette (not shown) which is placed within the endotracheal tube 10 to assist in its positioning.

Figure 7:
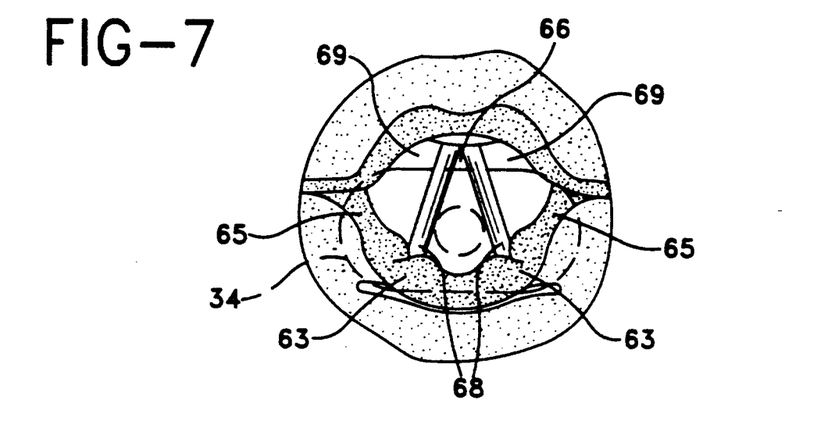
FIG. 7 is a top view of a patient's larynx having the shape of the present invention endotracheal tube flange superimposed over the picture to show how the present invention engages the larynx.

As the lower end 30 of the outer tube member 14 enters the patient's larynx, the shaped flange 34 where it contacts the arytenoid cartilages. The contact between the shaped flange 34 and the arytenoid cartilages stops the lower end 30 of the outer tube member 14 from being further advanced into the larynx. Since the shaped flange 34 contacts the arytenoid cartilages of the patient, the lower end 30 of the outer tube member 14 comes to rest in the larynx at a point just above the vocal cords of the patient. Referring to FIG. 7 in conjunction with FIGS. 5 and 6, it can be seen how the shaped flange 34 contacts the arytenoid cartilages by resting upon the cuneiform tubercles 63 between the aryepiglottic folds 65.

With the shaped flange 34 of the outer tube member 14 in contact with the arytenoid cartilages in the patient's larynx, the inner tube member 12 is positioned above the gap 66 in between the patient's vocal folds 68, i.e. the true vocal cords. Furthermore, the transition region 32 which extends below the shaped flange 34 on the lower end 30 of the outer tube ay member 14 extends into the gap 66 in between the vocal folds 68.

in the shown embodiment, the shaped flange 34 is shown to be substantially planar. It should be understood that the shaped flange 34 may be contoured to follow the shape of the arytenoid cartilages it contacts. Furthermore, it should also be understood that the size of the shaped flange 34 may be made so as to pass by the arytenoid cartilages and rest directly upon the ventricular folds 69, i.e. the false vocal cords. However, since contact with the ventricular folds 69 may cause inflammation of those tissues, it is preferred that the shaped flange 34 be sized to contact the arytenoid cartilages. The contact of the shaped flange 34 against the arytenoid cartilages allows the person administering the intubation the clearest view of the position of the shaped flange and spreads any forces, created by the presence of the flange 34, among the greatest available surface area. Furthermore, the positioning of the shaped flange 34 across the arytenoid cartilages acts as a baffle in the patient's airway. As such, the shaped flange 34 acts to reduce the occurrence of intubation gases exiting the larynx and entering the esophagus where gastric content aspiration can occur.

The distance between the position of the shaped flange 34 on the arytenoid cartilages of a patient and a patient's trachea can be readily determined for any sized patient. For example in a neonate, the length of the neonate larynx may only be one centimeter. With the shaped flange 34 of the outer tube member 14 resting within the patient's larynx, a baseline is formed from which very accurate measurements can be made. By advancing the inner tube member 12 within the outer tube member 14, the discharging end 20 of the inner tube member 12 extends beyond the lower end 30 of the outer tube member 14. The inner tube member 12 is narrow and as such is able to pass in between the vocal folds 68. Once through the vocal folds 68, the discharging end 20 of the inner tube member 12 enters the patient's trachea where aspiration can occur. As the inner tube member 12 is advanced into the patient's trachea the outer tube member 14 is held at its set position resting upon the patient's arytenoid cartilages. As such, the inner tube member 12 is moving relative the outer tube member 14. As has been previously described, the inner tube member 12 has a finger engagement support 38 attached to it that rides within an elongated slot 40 in the outer tube member 14. As the inner tube member 12 moves relative the outer tube member 14, the finger engagement support 38 moves within the slot 40 and the point indicator 44 on the finger engagement support 38 moves across the distance indicators 42 that are printed on the exterior of the outer tube member 14. By observing the relationship in between the point indicator 44 and the distance indicator 42, the person administering the intubation knows exactly where the discharge end 20 of the endotracheal tube is within the patient. Furthermore, by utilizing the locking means in between the inner tube member 12 and the outer tube member 14, the position of the discharging end 20 can be locked into any desired position in the patient's trachea.

By utilizing the point of contact between the shaped flange 34 and the patient's larynx as a base point, a person administering the intubation can be assured that the discharging end 20 of the endotracheal tube is not above or below the trachea but rather is properly locked into position within the trachea. Furthermore, the administration of the endotracheal tube 10 can be accomplished without having to check the position of the tube in the patient with an X-ray.

Figure 8:
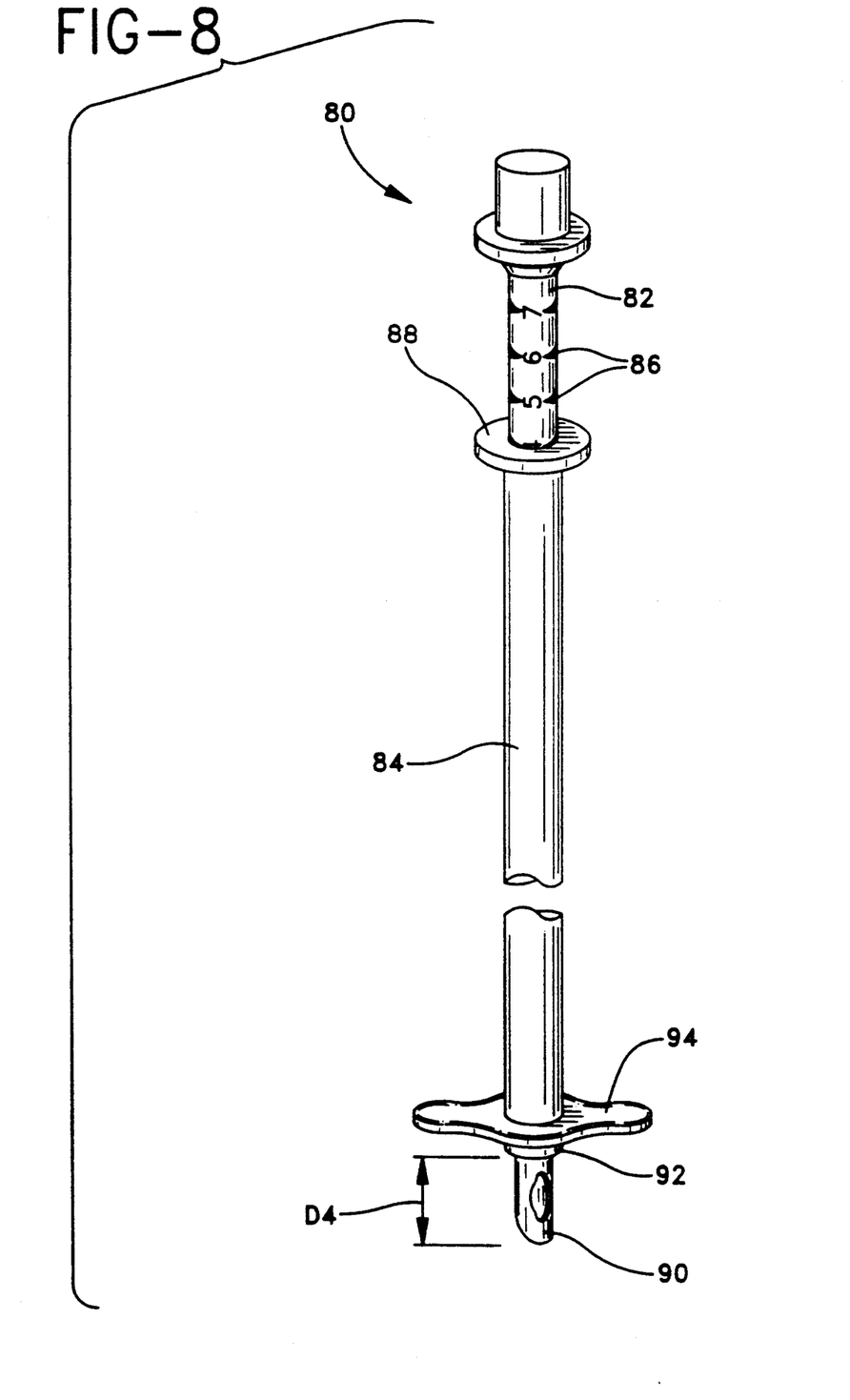
FIG. 8 is a front view of an alternative embodiment of the present invention endotracheal tube.

Referring now to FIG. 8, an alternative embodiment of the present invention endotracheal tube 80 is shown. In this embodiment, an inner tube member 82 is positioned within an outer tube member 84 with a slight interference fit. Consequently, the inner tube member 82 cannot be reciprocally moved within the outer tube member 84 unless subjected to a force that overcomes the frictional forces of the interference fit. In the shown embodiment, the interference fit thereby acts as a locking means, holding the inner tube member 82 into a desired set position relative the outer tube member 84. Since the shown endotracheal tube 80 does not have the finger activated locking member of the first described embodiment, distance indicators 86 are printed onto the inner tube member 82. By aligning the various distance indicators 86 with the upper end 88 of the outer tube member 84, a person administering the intubation procedure can determine how far the discharging end 90 of the inner tube member 82 extends below the bottom end 92 of the outer tube member 84. For instance in the shown embodiment of FIG. 8, the distance indicator 86 of four millimeters aligns with the upper end 88 of the inner tube member 82. Consequently, the distance D4 by which the discharging end 90 of the inner tube member 82 extends below the lower end 90 of the outer tube member 84 is equivalent to four millimeters.

In FIG. 8, the shaped flange 94 radially extending from the outer tube member 84 is not planar as it was in previous embodiments. Rather, the flange 94 is contoured. The contours of the flange 94 are formed to match the contours of the corniculate tubercles, aryepiglottic folds and other elements within the larynx upon which the flange 94 will come to rest. The contours of the surfaces of the larynx are known and therefore need not be set forth here in length except to say the flange 94 substantially conforms to those contours. By conforming in shape, the flange 94 can create a better seal across the larynx thereby better preventing the exit of gases from the larynx other than through the endotracheal tube 80.

Figure 9:
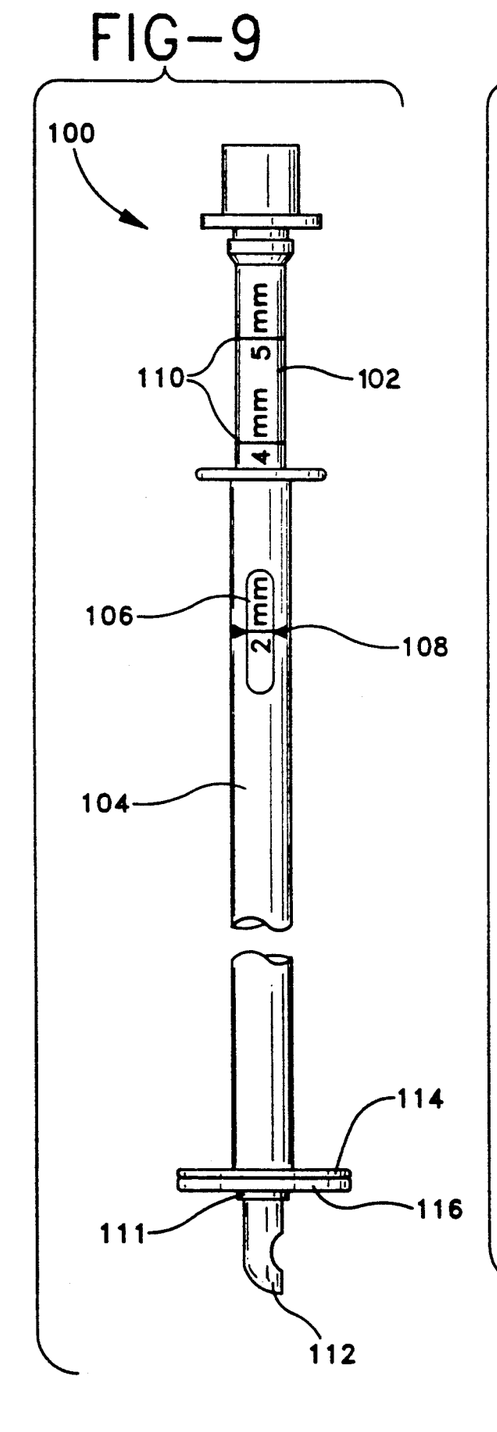
FIG. 9 is a front view of a second alternative embodiment of the present invention endotracheal tube.

Referring to FIG. 9, a second alternate embodiment of the present invention endotracheal tube 100 is shown. In this shown embodiment, the inner tube member 102 is positioned with a friction fit within the outer tube member 104 in the manner previously described in connection with FIG. 8. However with the shown embodiment, a window orifice 106 is formed through the outer tube member 104 allowing a segment of the inner tube member 102 to be clearly viewed. A point indicator 108 is printed on the outer tube member 104 at points adjacent the window orifice 106. By aligning the point indicator 108 to distance indicators 110 printed on the inner tube member 102, the person administering the intubation procedure is provided an indication as to how far the discharging end 112 of the inner tube member 102 extends below the bottom end 111 of the outer tube member 104.

In FIG. 9, the flange 114 extending from around the outer tube member 104 contains a downwardly extending cushioned region 116. The cushioned region 116 can be formed of elastomeric material or may be an air filled bladder. The cushioned region 116 contacts the larynx when the endotracheal tube 100 is administered to a patient. The cushioned region 116 thereby conforms to the contours of the larynx and softens the points of contact on the larynx leading to less aggravation of contacted tissues.

Figure 10:
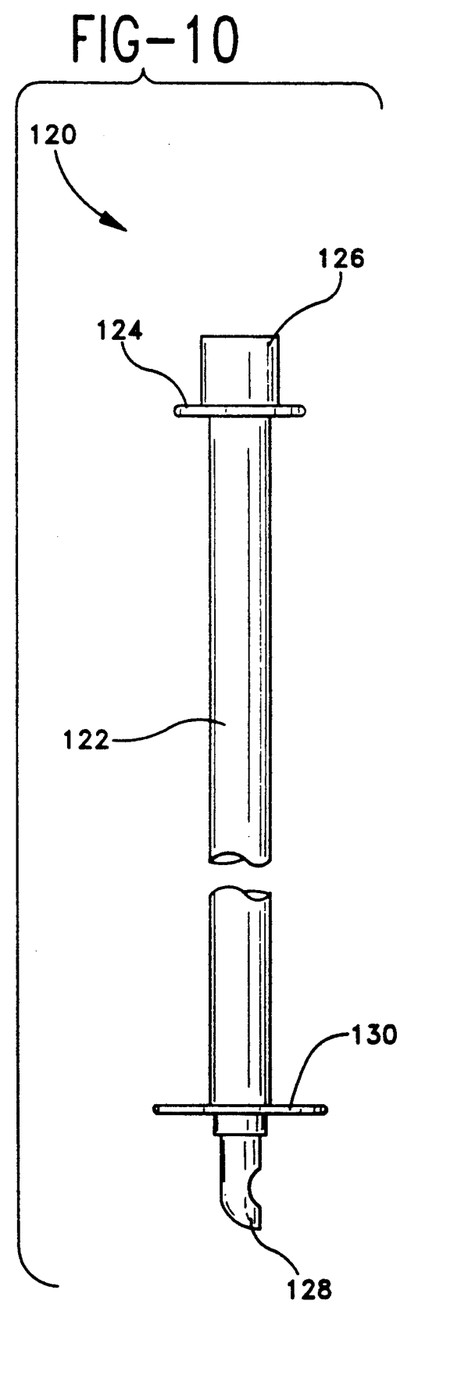
FIG. 10 is a front view of a third alternative embodiment of the present invention endotracheal tube.

Referring lastly to FIG. 10, a third alternative embodiment of the present invention endotracheal tube 120 is shown. In this embodiment there is only one unistructurally formed tube member 122. The tube member 122 has a gas receiving end 124 shaped to receive a gas line connector 126 and a discharging end 128 formed with the needed orifices to discharge gases into a patient's trachea. A flange 130 is formed proximate the discharging end 128. The flange 130 is formed to contact the larynx of a patient in the manners previously described. The discharging end 128 can be formed at any desired length below the flange 130, as such a person administering the intubation procedure will always know how far below the larynx the discharging end 128 extends.

For instance, if an anesthesiologist decides to intubate a neonate patient having a trachea that is positioned from one to three millimeters below the patient's larynx, the anesthesiologist can choose an endotracheal tube, such as is shown, wherein the discharging end 128 extends two millimeters below the flange 130. By using such an endotracheal tube, the proper positioning of the discharging end 128 in the trachea is essentially assured.

Although the described embodiments of the present invention are believed to represent the best modes of the invention, it should be understood that many described components of the present invention have known functional equivalents. Furthermore, proportions, materials and orientations used within the description can be modified by a person skilled in the art. Additionally, the features shown in the differing described embodiments of the present invention can be mixed and combined in as desired and need not be confined to the specific embodiments shown. All such modifications are intended to be covered by the scope of the invention as set forth in the appended claims.

What is claimed is:

1. An endotracheal tube comprising:
   a flexible outer tube member having a first and second open end, said second end of said outer tube member having a size narrow enough to be passed through the mouth of a patient towards the patient's larynx, wherein said second end engages said patient's larynx and is prevented from advancing past the vocal folds in the patient's larynx; and
   a flexible inner tube member having an open distal end and an open proximal end, said inner tube member being reciprocally movable within said outer tube member, wherein said distal end of said inner tube member can be selectively extended a desired distance beyond said second end of said outer tube member through said vocal folds and into the patient's trachea.

2. The endotracheal tube in accordance with claim 1 wherein said second end of said outer tube member includes a radially extending flange member, said flange member contacting the patient's larynx as said second end of said outer tube member is advanced within the patient, said flange member preventing the advancement of said second end beyond said larynx.

3. The endotracheal tube in accordance with claim 2 wherein said flange member is shaped to position said distal end of said inner tube member over the gap between said vocal folds of the patient's larynx as said flange member contacts said larynx.

4. The endotracheal tube in accordance with claim 2 wherein said flange member is shaped to substantially prevent the flow of gases through said larynx past said flange member other than through said inner tube member.

5. The endotracheal tube in accordance with claim 2 wherein said flange member is contoured to substantially match the curvatures of said larynx engaged by said flange member.

6. The endotracheal tube in accordance with claim 1 further including an indicating means for providing a visual indication indicative of the value of said desired distance.

7. The endotracheal tube in accordance with claim 1 further including a retaining means for retaining said inner tube at a desired position within said outer tube member.

8. The endotracheal tube in accordance with claim 1 wherein said second end of said outer tube member creates a substantially gas tight seal around said inner tube member thereby preventing the flow of gases in between said inner tube member and said outer tube member.

9. The endotracheal tube in accordance with claim 2 wherein said flange member includes a cushioned surface, said cushioned surface contacting said larynx and substantially conforming to the contours of said larynx, wherein said cushioned surface reduces trauma to said larynx.

10. An endotracheal tube for use in an intubation procedure wherein said endotracheal tube is introduced into the trachea of a patient past the vocal folds in a patient's larynx, said endotracheal tube comprising:
    a flexible conduit means having an open distal end and an open proximal end, thereby allowing the flow of gases therethrough, wherein said distal end is sized to fit between said vocal folds; and
    engagement means positioned a known distance from said distal end, said engagement means engaging said larynx at a plurality of points, preventing the advancement of said engagement means beyond said vocal folds within said larynx as said distal end is advanced toward the patient's trachea, said distal end thereby being positioned beyond said plurality of points by said known distance, whereby said distal end extends through and beyond said larynx into the patient's trachea.

11. The endotracheal tube according to claim 10 further including an adjustment means for selectively adjusting said know distance between said distal end and said engagement means.

12. The endotracheal tube according to claim 10 wherein said engagement means includes a flange radially extending from said flexible conduit means, said flange having larger width than the gap between vocal folds in the patient's larynx, thereby preventing the passage of said flange beyond said vocal folds.

13. The endotracheal tube according to claim 12 wherein said engagement means is contoured to substantially match the shape of said larynx where said engagement means contacts said larynx.

14. The endotracheal tube according to claim 10 wherein said engagement means includes a cushioned surface, said cushioned surface contacting said larynx and substantially conforming to the contours of said larynx.

15. The endotracheal tube according to claim 10 further including an indicating means for providing a visual indication indicative of the value of said known distance.

16. The endotracheal tube according to claim 11 further including a locking means for retaining said distal end at one desired distance beyond said engagement means.

17. A method of endotracheal intubation comprising:
    advancing an outer tube member into a patient's throat until said outer tube member contacts the larynx of the patient and the further advancement of said outer tube member is inhibited by the contact between said larynx and said outer tube member; and
    advancing an inner tube member a known distance beyond said outer tube member wherein said inner tube member extends through said larynx and into the trachea of the patient by a desired length.

18. The method according to claim 17 further including the step of locking said inner tube member in a set position relative said outer tube member.

19. The method according to claim 17 further including the step of creating a gas barrier above said larynx by the contact of said outer tube member with said larynx, said gas barrier substantially hindering the passage of gas in or out of said larynx other than through said inner tube member.

20. The method according to claim 17 further including the step of providing a visual indication indicative of said desired length said inner tube member extends into the trachea of the patient.

21. A method of endotracheal intubation, comprising the steps of:
   providing a flexible conduit having an open first and second end and having an engagement means disposed between said first and second end a predetermined distance from said second end;
   advancing said second end through a patient's mouth toward the patient's trachea, wherein said engagement means engages the larynx of the patient and prevents the further advancement of said second end, whereby said second end is positioned beyond said trachea and into the patient's trachea by said predetermined distance.

22. The method according to claim 21, further including the step of creating a gas barrier by the contact of said engagement means with said larynx, said gas barrier substantially hindering the passage of gas in and out of the trachea other than through said flexible conduit.

* * * * *